United States Patent [19]

May et al.

[11] 4,269,990

[45] May 26, 1981

[54] 1-ACYL-2-IMIDAZOLINES AND THEIR MANUFACTURE

[75] Inventors: Hans-Joachim May, Neustadt; Horst Koenig, Ludwigshafen, both of Fed. Rep. of Germany

[73] Assignee: BASF Aktiengesellschaft, Fed. Rep. of Germany

[21] Appl. No.: 100,655

[22] Filed: Dec. 5, 1979

Related U.S. Application Data

[63] Continuation of Ser. No. 31,032, Apr. 18, 1979, abandoned, which is a continuation of Ser. No. 846,814, Oct. 31, 1977, abandoned.

[30] Foreign Application Priority Data

Nov. 15, 1976 [DE] Fed. Rep. of Germany ....... 2652004

[51] Int. Cl.³ ................. C07D 233/50; C07D 401/06; C07D 405/06; C07D 409/06
[52] U.S. Cl. .................................... 548/315; 548/316; 546/278; 542/439; 542/440
[58] Field of Search ................ 548/315, 316; 542/439, 542/440; 546/278

[56] References Cited

U.S. PATENT DOCUMENTS

| | | | |
|---|---|---|---|
| 3,288,805 | 11/1966 | Berg | 548/315 |
| 3,636,219 | 1/1972 | Culik et al. | 548/315 |
| 3,931,216 | 1/1976 | Franzmair | 548/315 |
| 3,988,345 | 10/1976 | Franzmair | 548/315 |

FOREIGN PATENT DOCUMENTS 741947 5/1970 Belgium .

*Primary Examiner*—Henry R. Jiles
*Assistant Examiner*—Natalia Harkaway
*Attorney, Agent, or Firm*—Keil & Witherspoon

[57] ABSTRACT

The invention relates to 1-acyl-2-imidazolines, processes for their manufacture, and their use as intermediates.

6 Claims, No Drawings

1-ACYL-2-IMIDAZOLINES AND THEIR MANUFACTURE

This is a continuation, division, of application Ser. No. 31,032, filed Apr. 18, 1979, now abandoned, which is a continuation of Ser. No. 846,814, filed Oct. 31, 1977, now abandoned.

The present invention relates to 1-acyl-2-imidazolines, processes for their manufacture and their use as intermediates.

An article by H. Bredereck et al (Chem. Ber. 92 (1959), 837 et seq.) discloses that fatty acid N,N-dialkylamides can be reacted with phosphorus oxytrichloride to give fatty acid N,N-dialkylamide/phosphorus oxytrichloride adducts, which react with amines to give tri-substituted amidines. H. and K. Bredereck further discloses (Chem. Ber. 94 (1961), 2278) that lactams, eg. 2-pyrrolidone, 2-piperidone, ε-caprolactam and 3,4-dihydro-2-quinolone, behave similarly and give semicyclic amidines. 1-Acyl-2-imidazolinones, for example, can also be obtained by this reaction (German Laid-Open Application DOS 2,316,377).

We have found, surprisingly, that 1-acyl-2-imidazolines of the general formula I

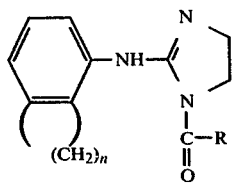

where n is 3 or 4 and R is hydrogen, alkyl of 1 to 4 carbon atoms (which is unsubstituted or is monosubstituted, disubstituted or trisubstituted by halogen, especially fluorine, chlorine or bromine, alkoxy of 1 to 4 carbon atoms, alkoxycarbonyl, where alkyl is of 1 or 2 carbon atoms, or phenoxy), cycloalkyl of 3 to 7 carbon atoms in the ring, alkoxy (where alkyl is of 1 to 8 carbon atoms, and which is unsubstituted or monosubstituted, disubstituted or trisubstituted by halogen, especially chlorine or bromine, or monosubstituted by alkoxy of 1 to 4 carbon atoms), cycloalkoxy of 3 to 10 carbon atoms in the ring (which is unsubstituted or substituted by alkyl of 1 to 4 carbon atoms), alkenyloxy of 3 or 4 carbon atoms, alkoxycarbonyl, where alkyl is of 1 or 2 carbon atoms, aralkoxy (which is unsubstituted or substituted in the aromatic portion by alkoxy of 1 to 4 carbon atoms, halogen, especially chlorine or bromine, or nitro), aryloxy (which is unsubstituted or substituted in the aromatic portion by nitro), phenyl and phenylalkyl of 7 or 8 carbon atoms (where phenyl is unsubstituted or monosubstituted, disubstituted or trisubstituted by alkyl of 1 to 4 carbon atoms, trifluoromethyl, halogen, especially chlorine, bromine and fluorine, alkoxy of 1 to 4 carbon atoms, alkylenedioxy of 3 to 5 carbon atoms or phenyl), phenylalkenyl of 8 or 9 carbon atoms (which is unsubstituted or monosubstituted, disubstituted or trisubstituted by halogen, especially fluorine, chlorine or bromine, or alkoxy of 1 to 4 carbon atoms), or a heterocyclic ring system, eg. thienyl, furyl or pyridyl, the pyridine ring being unsubstituted or substituted by halogen, especially chlorine, are valuable intermediates for the manufacture of the corresponding 1-unsubstituted imidazolines, because of their ready accessibility and their ease of hydrolysis.

Examples of alkyl R are methyl, ethyl, propyl and butyl, whilst examples of substituted alkyl R are monohalomethyl, monohaloethyl, trihalomethyl, methoxyethyl, ethoxyethyl, phenoxymethyl, nitrophenoxymethyl, methoxycarbonylmethyl and ethoxycarbonylmethyl.

Examples of cycloalkyl R are cyclopropyl, cyclobutyl, cyclopentyl, cyclohexyl and cycloheptyl.

Examples of alkoxy radicals R, which may be unsubstituted or substituted by one or more halogen atoms or an alkoxy radical are methoxy, ethoxy, propoxy, butoxy, amyloxy, 2-ethylhexoxy, bromoethoxy, trichloroethoxy and methoxyethoxy.

Examples of cycloalkoxy radicals R are cyclopentoxy, cyclohexoxy and tert.-butylcyclohexoxy.

An example of alkenyloxy R is allyloxy.

Examples of alkoxycarbonyl R are methoxycarbonyl and ethoxycarbonyl.

Examples of aralkoxy R, which is unsubstituted or substituted in the aromatic structure by alkoxy, halogen or nitro, are benzyloxy, methoxybenzyloxy, chlorobenzyloxy and nitrobenzyloxy.

Examples of aroxy R are phenoxy and nitrophenoxy.

Examples of phenyl R, which may be unsubstituted or substituted by one or more alkyl, haloalkyl, halogen, alkoxy, alkylenedioxy or phenyl are methylphenyl, ethylphenyl, propylphenyl, trifluoromethylphenyl, fluorophenyl, chlorophenyl, bromophenyl, methoxyphenyl, ethoxyphenyl, propyloxyphenyl, butyloxyphenyl, biphenylyl, dimethylphenyl, chloromethylphenyl, dichlorophenyl, dimethoxyphenyl, methoxyethoxyphenyl, diethoxyphenyl, methylenedioxyphenyl, ethylenedioxyphenyl, trimethoxyphenyl, dimethoxyethoxyphenyl and triethoxyphenyl.

Examples of phenylalkyl R, which may be substituted in the aromatic structure by one or more of the radicals alkyl, halogen, alkoxy and alkylenedioxy are benzyl, methylbenzyl, chlorobenzyl, methoxybenzyl, dimethylbenzyl, dichlorobenzyl, dimethoxybenzyl, methylenedioxybenzyl, ethylenedioxybenzyl, trimethoxybenzyl, phenylethyl, chlorophenylethyl, methoxyphenylethyl, dichlorophenylethyl and dimethoxyphenylethyl.

Examples of phenylalkenyl R are styryl, methylstyryl, propylstyryl, chlorostyryl, fluorostyryl, methoxystyryl, dichlorostyryl, dimethoxystyryl, methylendioxystyryl and trimethoxystyryl.

Examples of heterocyclic ring systems R are thienyl, furyl, pyridyl and chloropyridyl.

Amongst the above meanings of R, the following are preferred: hydrogen; alkyl of 1 to 4 carbon atoms, eg. methyl, ethyl, propyl, i-propyl, n-butyl, i-butyl, sec.-butyl and tert.-butyl; alkyl substituted by from one to three chlorine, bromine or fluorine atoms, one alkoxy or alkoxycarbonyl radical, alkyl being in each case of 1 or 2 carbon atoms, or phenoxy (which is unsubstituted or substituted by nitro), eg. chloromethyl, trichloromethyl, trifluoromethyl, 2-chloroethyl, 2-methoxyethyl, 2-ethoxyethyl, phenoxymethyl, p-nitrophenoxymethyl, methoxycarbonylmethyl and ethoxycarbonylmethyl; cycloalkyl of 3 to 6 carbon atoms in the ring, eg. cyclopropyl, cyclopentyl and cyclohexyl; alkoxy of 1 to 8 carbon atoms, which is unsubstituted or substituted by from 1 to 3 bromine or chlorine atoms or one alkoxy group of 1 or 2 carbon atoms, eg. methoxy, ethoxy, propoxy, i-propoxy, n-butoxy, i-butoxy, sec.-butoxy, amyloxy, 2-ethylhexoxy, 2-bromoethoxy, 2,2,2- trichloroethoxy and 2-methoxyethoxy; cycloalkoxy of 5 or 6 ring members, the cycloalkyl radical being unsubstituted or substituted by alkyl of 1 to 4 carbon atoms, eg. cyclopentoxy, cyclohexoxy and 4-tert.-butylcyclohexoxy; alkenyloxy of 3 or 4 carbon atoms, eg. allyloxy; alkoxycarbonyl, eg. methoxycarbonyl and ethoxycarbonyl; benzyloxy, in which phenyl is unsubstituted or substituted by chlorine, methoxy or nitro, eg. benzyloxy, p-methoxybenzyloxy, p-chlorobenzyloxy and p-nitrobenzyloxy; phenoxy, in which phenyl is unsubstituted or substituted by nitro, eg. phenoxy and p-nitrophenoxy; phenyl which is unsubstituted or carries from 1 to 3 substituents chosen from amongst fluorine, chlorine or bromine atoms, alkyl of 1 to 4 carbon atoms or alkoxy of 1 to 4 carbon atoms, or is monosubstituted by trifluoromethyl, phenyl, methylenedioxy or ethylenedioxy, eg. phenyl, methylphenyl, ethylphenyl, propylphenyl, i-propylphenyl, trifluoromethylphenyl, fluorophenyl, chlorophenyl, bromophenyl, methoxyphenyl, ethoxyphenyl, propyloxyphenyl, i-propyloxyphenyl, n-butyloxyphenyl, biphenylyl, dimethylphenyl, methylchlorophenyl, dichlorophenyl, dimethoxyphenyl, ethoxymethoxyphenyl, diethoxyphenyl, methylenedioxyphenyl, ethylenedioxyphenyl, trimethoxyphenyl and triethoxyphenyl; phenylalkyl of 7 or 8 carbon atoms, in which phenyl is unsubstituted or is monosubstituted, disubstituted or trisubstituted by chlorine or bromine, alkoxy of 1 to 3 carbon atoms or alkyl of 1 or 2 carbon atoms or is monosubstituted by methylenedioxy or ethylenedioxy, eg. benzyl, methylbenzyl, chlorobenzyl, methoxybenzyl, dimethylbenzyl, dichlorobenzyl, dimethoxybenzyl, methylenedioxybenzyl, ethylenedioxybenzyl, trimethoxybenzyl, 1-phenylethyl, 1-o-methoxyphenylethyl, 1-p-chlorophenylethyl, 2-phenylethyl, 2-chlorophenylethyl, 2-(methoxyphenyl)-ethyl and 2-(dimethoxyphenyl)-ethyl; styryl, which is unsubstituted or monosubstituted, disubstituted or trisubstituted by an alkyl of 1 to 3 carbon atoms, a halogen atom, especially fluorine, chlorine or bromine atom, an alkoxy radical of 1 to 3 carbon atoms or a methylenedioxy radical, eg. styryl, methylstyryl, i-propylstyryl, chlorostyryl, fluorostyryl, methoxystyryl, dischlorostyryl, dimethoxystyryl, methylenedioxystyryl and trimethoxystyryl; and a heterocyclic ring, eg. thienyl, furyl, pyridyl, and chloropyridyl.

Amongst these, the particularly preferred meanings of R are alkyl of 1 to 4 carbon atoms, especially methyl and ethyl, alkoxy, where alkyl is of 1 to 8 carbon atoms, especially methoxy and ethoxy, and phenyl.

The compounds of the invention can be manufactured by reacting an amine of the general formula II

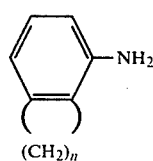

where n has the above meaning, with a 1-acyl-2-imidazolidinone of the general formula III

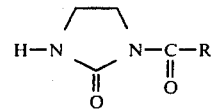

where R has the above meaning, in the presence of at least 1 mole of phosphorus oxytrichloride at from 20° to 120° C. The preferred reaction temperatures are from 40° to 70° C. Experience has shown that the reaction is advantageously carried out with from two to three times the molar amount of phosphorus oxychloride. In addition, further phosphorus oxychloride may or may not be used as a solvent.

The reaction of an amine of the general formula II with a 1-acyl-2-imidazolidinone of the general formula III is preferably carried out with a molar ratio of from 1:1.1 to 1:1.5, and in addition is advantageously carried out in excess POCl$_3$ as the solvent, preferably at from 40° to 70° C. or at the reflux temperature of any solvent which may be used. When POCl$_3$ is employed as the solvent, its amount is advantageously up to a 20-molar excess. In some cases the amount used is determined by the need to ensure that the reaction mixture should remain easily stirrable. The reaction can also be carried out advantageously in the presence of an inert organic solvent, for example a chlorohydrocarbon, eg. chloroform or carbon tetrachloride. Furthermore, it is advantageous to heat the mixture in an inert atmosphere, eg. under nitrogen or argon, because of the relative ease with which the amines used can oxidize.

After completion of the reaction (which may be followed by, for example, thin layer chromatography), the excess POCl$_3$ is removed by distillation, and after neutralization the resulting compounds of the invention, having the general formula I, may be purified by physical methods, eg. partition, crystallization or chromatography, or by chemical methods, eg. forming salts, crystallizing these and then decomposing them in an alkaline medium. In purifying the products, the nature of the anion of the salt is immaterial, since all that matters is that the salt should be well defined and readily crystallizable.

The excess POCl$_3$ is preferably distilled off, and in order to avoid decomposing the reaction product it is particularly preferred that the distillation is carried out under reduced pressure. The distillation residue obtained is mixed with cold water, preferably ice water, an aqueous alkaline solution, eg. of sodium bicarbonate, sodium carbonate or sodium hydroxide, is added until the mixture reacts distinctly alkaline, and the batch is preferably extracted with a water-immiscible solvent, eg. methylene chloride or chloroform. After removing the solvent, the substances of the invention, having the formula I, are preferably purified by crystallization from an inert organic solvent, eg. hexane, cyclohexane, toluene, isopropanol or acetonitrile.

The 1-acyl-2-imidazolidinones of the formula III, used as starting compounds, can be obtained by acylating ethyleneurea with carboxylic acid anhydrides or with carboxylic acid halides, in the presence or absence of acid-binding agents, eg. triethylamine, pyridine or antipyrine, in the conventional manner; good yields are obtained. Some of the 1-acyl-2-imidazolidinones are described in, for example, German Laid-Open Applications DOS No. 2,152,967 and 2,316,377.

The 1-acyl-2-imidazolines according to the invention, of the general formula I, are valuable intermediates for the manufacture of imidazolines of the general formula IV

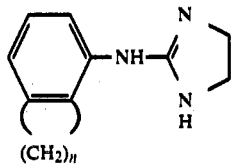

where n is 3 or 4, which compounds are useful drugs.

We have found, surprisingly, that elimination of the acyl radical from the compounds according to the invention, of the general formula I, is achievable by merely heating in water, preferably by refluxing, whilst elimination of the acyl group from the chemically similar 1-acyl-2-arylamino-2-imidazolines, manufactured, for example, by the process of German Laid-Open Application DOS No. 2,316,377, is only achievable with acid or alkaline reagents and in lower aliphatic alcohols as solvents. Using the intermediates according to the invention provides an improvement over the methods described in German Laid-Open Application DOS No. 2,316,377, both in respect of the cheapness of the hydrolytic agent used and in respect of the yields achieved.

The advantageous process for deacylating a compound of the formula I is characterized in that a mixture of the compound with water is heated at from 70° to 100° C., with or without passing steam through the mixture. As a rule, from 10 to 25% strength by weight mixtures with water are used. The amount of water is advantageously chosen to allow the system to be stirred readily. Steam distillation is particularly advantageous for removing unconverted amine, which, if not removed in this way, may become difficult to remove by crystallization.

The deacylated compound can be manufactured by using the aqueous solution of the acylated compound directly, without having to remove troublesome reagents. The imidazoline can advantageously be obtained from the resulting aqueous solution of the imidazoline bases of the formula IV by converting it to the sparingly soluble nitrate, which separates out in a crystalline form, which is isolated. The imidazoline nitrates are obtained in a high yield and virtually analytically pure.

In order to be able to carry out the deacylation or hydrolysis by heating in water, the acyl-imidazolines according to the invention need not be isolated as such. It suffices to remove the excess POCl$_3$ by distillation, take up the evaporation in a suitable extractant, for example a chlorohydrocarbon, eg. chloroform, bring the pH to about 11 with an alkali solution, eg. sodium hydroxide solution, free the extract, which has been washed neutral with water, from the solvent and reflux the residue with water as described. It has proved particularly advantageous to pass steam into the reaction mixture at the same time, so that unconverted amine of the formula II passes over with the steam and, being the most valuable of the starting materials employed, can be recovered from the distillate.

Deacylation in water is in principle possible with all 1-acyl-2-imidazolines according to the invention, of the general formula I. Naturally, it is a precondition that they should be sufficiently water-soluble at the temperatures employed. Solubilizing agents may or may not be added in order to increase the solubility of the compounds in water. Because of their cheapness, ready accessibility, relatively good solubility in water and relatively rapid hydrolysis, the compounds of the formula I, where R is alkyl of 1 to 4 carbon atoms, especially methyl or ethyl, alkoxy of 1 to 8 carbon atoms, especially methoxy or ethoxy, or phenyl, are particularly preferred. In these compounds, the deacylation in aqueous solution at 100° C. is complete after from 2 to 4 hours.

Preferred starting compounds for the deacylation reaction are, accordingly, 1-acetyl-, 1-propionyl-, 1-methoxycarbonyl-, 1-ethoxycarbonyl- and 1-benzoyl-2-(4-indanylamino)-2-imidazoline and the corresponding 5,6,7,8-tetrahydro-1-naphthyl-amino compounds of the formula I.

The process for the manufacture of 2-arylamino-2-imidazolines by hydrolysis of 1-acyl-2-imidazolines is of particular importance since, in contrast to conventional processes for the manufacture of 2-arylamino-2-imidazolines, it does not require any organo-sulfur compounds which could pollute the environment in the course of the synthesis, and since furthermore the most valuable starting material, ie. the amine of the general formula II, is only employed toward the end of the reaction sequence, thereby giving the best overall yield of imidazolines of the formula IV, based on amine converted. The conventional methods which can be used for the manufacture of 2-arylamino-2-imidazolines of the general formula V (German Pat. Nos. 1,191,381, 1,195,323 and 2,136,325) entail organo-sulfur intermediates, eg. thioureas or isothiuronium compounds, from which hydrogen sulfide or mercaptan is eliminated in the course of the cyclizing reaction.

It should be pointed out that the compounds according to the invention, of the general formula I, as well as the 2-imidazolines of the formula IV, can be present partially or completely in a second tautomeric form of the formula Ia:

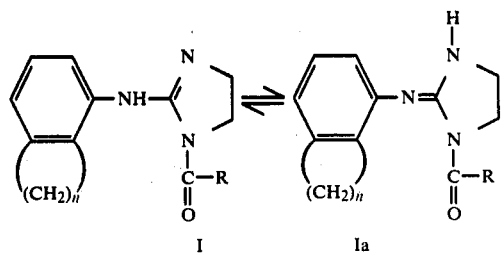

The Examples which follow illustrate the invention without implying any limitation.

EXAMPLE 1

140.9 g (1.1 moles) of 1-acetyl-2-imidazolidinone (melting point 186°-187° C.) are introduced into 1,320 ml of POCl$_3$ and 133.2 g (1 mole) of 4-amino-indan are added dropwise, with vigorous stirring, under conditions such that the internal temperature does not rise above 50° C. After completion of the addition, stirring is continued for 40 hours at 50° C. The excess POCl$_3$ is then distilled off as completely as possible under reduced pressure on a rotary evaporator and the distillation residue is added to 5 l of ice water whilst keeping the temperature at ≦15° C. by further addition of ice. The pH is brought to 11 by means of 25% strength sodium hydroxide solution, whilst cooling with ice, the mixture is repeatedly extracted with chloroform, the combined chloroform phases are again washed with 1 liter of 2 N sodium hydroxide solution and are then washed neutral with water and dried over anhydrous sodium sulfate, and the chloroform is distilled off. The residue is recrystallized from isopropanol. 84.3 g of pure 1-acetyl-(4-indanylamino)-2-imidazoline of melting point 180.5°–182° C. are obtained.

70 g of 4-amino-indan are recovered from the recrystallization mother liquor.

The yield of 1-acetyl-(4-indanylamino)-2-imidazoline is 73.1% of theory (based on 4-amino-indan converted).

The following compounds were also obtained by the process described in Example 1:

EXAMPLE 2

From 1-propionyl-2-imidazolidinone (melting point 148°–149° 1 C.) and 4-amino-indan: 1-propionyl-2-(4-indanylamino)-2-imidazoline, melting point 156°–157° C.

EXAMPLE 3

From 1-n-butyryl-2-imidazolidinone (melting point 104°–106° C.) and 4-amino-indan: 1-n-butyryl-2-(4-indanylamino)-2-imidazole, melting point 77°–80° C.

EXAMPLE 4

From 1-trifluoroacetyl-2-imidazolidinone (melting point 160°–164° C.) and 4-amino-indan: 1-trifluoroacetyl-2-(4-indanylamino)-2-imidazoline, melting point 149.5°–152° C.

EXAMPLE 5

From 1-formyl-2-imidazolidinone (melting point 156°–158° C.) and 4-amino-indan: 1-formyl-2(4-indanylamino)-2-imidazoline, melting point 166°–167° C.

EXAMPLE 6

From 1-ethoxycarbonyl-2-imidazolidinone (melting point 124°–126° C.) and 4-amino-indan: 1-ethoxycarbonyl-2-(4-indanylamino)-2-imidazoline, melting point 102°–103° C.

EXAMPLE 7

From 1-acetyl-2-imidazolidinone and 5,6,7,8-tetrahydro-1-naphthylamine: 1-acetyl-2-(5,6,7,8-tetrahydro-1-naphthylamino)-2-imidazoline, melting point 175.5°–176.5° C.

EXAMPLE 8

From 1-benzoyl-2-2-imidazolidinone (melting point 169°–171° C.) and 4-amino-indan: 1-benzoyl-2-(4-indanylamino)-2-imidazoline, melting point 194°–197° C.

EXAMPLE 9

From 1-benzoyl-2-2-imidazolidinone and 5,6,7,8-tetrahydro-1-naphthylamine: 1-benzoyl-2-(5,6,7 8-tetrahydro-1-naphthylamino)-2-imidazoline, melting point 163°–165° C.

EXAMPLE 10

From 1-(o-toluoyl)-2-imidazolidinone (melting point 234°–236.5° C.) and 4-amino-indan: 1-(o-toluoyl)-2-(4-indanylamino)-2-imidazoline, melting point 247°–249° C.

EXAMPLE 11

From 1-(o-chlorobenzoyl)-2-imidazolidinone (melting point 124°–125.5° C.) and 4-amino-indan: 1-(o-chlorobenzoyl)-2-(4-indanylamino)-2-imidazoline, melting point 186°–187° C.

EXAMPLE 12

From 1-(m-chlorobenzoyl)-2-imidazolidinone (melting point 189°–191° C.) and 4-amino-indan: 1-(m-chlorobenzoyl)-2-(4-indanylamino)-2-imidazoline, melting point 153°–156° C.

EXAMPLE 13

From 1-(p-toluoyl)-2-imidazolidinone (melting point 188°–192° C.) and 4-amino-indan: 1-(p-toluoyl)-2-(4-indanylamino)-2-imidazoline, melting point 148°–149° C.

EXAMPLE 14

From 1-(p-toluoyl)-2-imidazolidinone and 5,6,7,8-tetrahydro-1-naphthylamine: 1-(p-toluoyl)-2-(5,6,7,8-tetrahydro-1-naphthylamino)-2-imidazoline, melting point 128°–130° C.

EXAMPLE 15

From 1-(p-isopropylbenzoyl)-2-imidazolidinone (melting point 165°–166.5° C.) and 4-amino-indan: 1-(p-isopropylbenzoyl)-2-(4-indanylamino)-2-imidazoline, melting point 167°–168° C.

EXAMPLE 16

From 1-(p-chlorobenzoyl)-2-imidazolidinone (melting point 204°–205.5° C.) and 4-amino-indan: 1-(p-chlorobenzoyl)-2-(4-indanylamino)-2-imidazoline, melting point 185°–186.5° C.

EXAMPLE 17

From 1-(p-fluorobenzoyl)-2-imidazolidinone (melting point 177°–180° C.) and 4-amino-indan: 1-(p-fluorobenzoyl)-2-(4-indanylamino)-2-imidazoline, melting point 207.5°–209° C.

EXAMPLE 18

From 1-(p-methoxybenzoyl)-2-imidazolidinone (melting point 167°–168° C.) and 4-amino-indan: 1-(p-methoxybenzoyl)-2-(4-indanylamino)-2-imidazoline, melting point 132.5°–134° C.

EXAMPLE 19

From 1-(p-ethoxybenzoyl)-2-imidazolidinone (melting point 182°–183.5° C.) and 4-amino-indan: 1-(p-ethoxybenzoyl)-2-(4-indanylamino)-2-imidazoline, melting point 148°–149.5° C.

EXAMPLE 20

From 1-(p-n-butyloxybenzoyl)-2-imidazolidinone (melting point 171.5°–173° C.) and 4-amino-indan: 1-(p-n-butyloxybenzoyl)-2-(4-indanylamino)-2-imidazoline, melting point 141°–142.5° C.

EXAMPLE 21

From 1-(4-biphenylylcarbonyl)-2-imidazolidinone (melting point >250° C.) and 4-amino-indan: 1-(p-biphenylylcarbonyl)-2-(4-indanylamino)-2-imidazoline, melting point 164°–165.5° C.

EXAMPLE 22

From 1-(2,6-dichlorobenzoyl)-2-imidazolidinone (melting point 228°–229.5° C.) and 4-amino-indan: 1-(2,6-dichlorobenzoyl)-2-(4-indanylamino)-2-imidazoline, melting point 167°–168° C.

EXAMPLE 23

From 1-(3,4-dimethoxybenzoyl)-2-imidazolidinone (melting point 182°–184° C.) and 4-amino-indan: 1-(3,4-dimethoxybenzoyl)-2-(4-indanylamino)-2-imidazoline, melting point 219°–221° C.

EXAMPLE 24

From 1-(3,4-methylenedioxybenzoyl)-2-imidazolidinone (melting point 167.5°–171° C.) and 4-amino-indan: 1-(3,4-methylenedioxybenzoyl)-2-(4-indanylamino)-2-imidazoline, melting point 157°–159° C.

EXAMPLE 25

From 1-(2,3,4-trimethoxybenzoyl)-2-imidazolidinone (melting point 156°–158° C.) and 4-amino-indan: 1-(2,3,4-trimethoxybenzoyl)-2-(4-indanylamino)-2-imidazoline, melting point 160°–162° C.

EXAMPLE 26

From 1-(3,4,5-trimethoxybenzoyl)-2-imidazolidinone (melting point 162°–163° C.) and 4-amino-indan: 1-(3,4,5-trimethoxybenzoyl)-2-(4-indanylamino)-2-imidazoline, melting point 167°–168.5° C.

EXAMPLE 27

From 1-(3,4,5-trimethoxybenzoyl)-2-imidazolidinone and 5,6,7,8-tetrahydro-1-naphthylamine: 1-(3,4,5-trimethoxybenzoyl)-2-(5,6,7,8-tetrahydro-1-naphthylamino)-2-imidazoline, melting point 153°–154° C.

EXAMPLE 28

From 1-phenylacetyl-2-imidazolidinone (melting point 112°–113.5° C.) and 4-amino-indan: 1-phenylacetyl-2-(4-indanylamino)-2-imidazoline, melting point 142°–144° C.

EXAMPLE 29

From 1-cinnamoyl-2-imidazolidinone (melting point 203°–205° C.) and 4-amino-indan: 1-cinnamoyl-2-(4-indanylamino)-2-imidazole, melting point 162°–164° C.

The following compounds can be obtained by the method described in Example 1:

EXAMPLE 30

1-(3,4-Dimethoxybenzoyl)-2-(4-indanylamino)-2-imidazoline, melting point 177°–178.5° C.

EXAMPLE 31

1-(2,6-Dimethylbenzoyl)-2-(4-indanylamino)-2-imidazoline, melting point 242°–244° C.

EXAMPLE 32

1-(2,6-Dimethoxybenzoyl)-2-(4-indanylamino)-2-imidazoline, melting point 245°–247° C.

EXAMPLE 33

1-(o-Tolylacetyl)-2-(4-indanylamino)-2-imidazoline, melting point 178°–180° C.

EXAMPLE 34

1-(o-Tolylacetyl)-2-(4-indanylamino)-2-imidazoline, melting point 179°–181° C.

EXAMPLE 35

1-(o-Methoxyphenylacetyl)-2-(4-indanylamino)-2-imidazoline, melting point 140°–141° C.

EXAMPLE 36

1-(m-Methoxyphenylacetyl)-2-(4-indanylamino)-2-imidazoline, melting point 139°–140° C.

EXAMPLE 37

1-(p-Methoxyphenylacetyl)-2-(4-indanylamino)-2-imidazoline, melting point 193.5°–195° C.

EXAMPLE 38

1-(p-Chlorophenylacetyl)-2-(4-indanylamino)-2-imidazoline, melting point 172°–173° C.

EXAMPLE 39

1-(2,6-Dichlorophenylacetyl)-2-(4-indanylamino)-2-imidazoline, melting point 180°–181° C.

EXAMPLE 40

1-(3,4-Methylenedioxyphenylacetyl)-2-(4-indanylamino)-2-imidazoline, melting point 177°–179° C.

EXAMPLE 41

1-(3,4-Ethylenedioxyphenylacetyl)-2-(4-indanylamino)-2-imidazoline, melting point 207°–209° C.

EXAMPLE 42

1-(3,4,5-Trimethoxyphenylacetyl)-2-(4-indanylamino)-2-imidazoline, melting point 164°–166° C.

EXAMPLE 43

1-(2-Phenylpropionyl)-2-(4-indanylamino)-2-imidazoline, melting point 148.5°–150° C.

EXAMPLE 44

1-[2-(o-Methoxyphenyl)-propionyl]-2-(4-indanylamino)-2-imidazoline, melting point 142°–143° C.

EXAMPLE 45

1-(2-p-Chlorophenyl-propionyl)-2-(4-indanylamino)-2-imidazoline, melting point 144°–145° C.

EXAMPLE 46

1-(3-p-Methoxyphenyl-propionyl)-2-(4-indanylamino)-2-imidazoline, melting point 159°–160.5° C.

EXAMPLE 47

1-[3-(3,4-Dimethoxyphenyl)-propionyl]-2-(4-indanylamino)-2-imidazoline, melting point 137°–139° C.

EXAMPLE 48

1-Benzyloxycarbonyl-2-(4-indanylamino)-2-imidazoline, melting point 124°–126° C.

EXAMPLE 49

1-Phenoxycarbonyl-2-(4-indanylamino)-2-imidazoline, melting point 144°–147° C.

EXAMPLE 50

1-(2-Thenoyl)-2-(4-indanylamino)-2-imidazoline, melting point 157°–158.5° C.

EXAMPLE 51

1-(3-Thenoyl)-2-(4-indanylamino)-2-imidazoline, melting point 150°–151.5° C.

EXAMPLE 52

1-Nicotinoyl-2-(4-indanylamino)-2-imidazoline, melting point 132°–133° C.

EXAMPLE 53

1-(6-Chloronicotinoyl)-2-(4-indanylamino)-2-imidazoline, melting point 176°–177.5° C.

EXAMPLE 54

1-(3-Pyridylacetyl)-2-(4-indanylamino)-2-imidazoline, melting point 157°–158.5° C.

EXAMPLE 55

1-(m-Toluoyl)-2-(4-indanylamino)-2-imidazoline, melting point 158°–160° C.

EXAMPLE 56

1-Isobutyryl-2-(4-indanylamino)-2-imidazoline, melting point 156°–157° C.

EXAMPLE 57

1-Methoxycarbonyl-2-(4-indanylamino)-2-imidazoline, melting point 131°–133° C.

EXAMPLE 58

1-Ethoxalyl-2-(4-indanylamino)-2-imidazoline, melting point 162°–166° C.

EXAMPLE 59

1-Cyclohexylcarbonyl-2-(4-indanylamino)-2-imidazoline, melting point 147°–149° C.

EXAMPLE 60

1-(m-Trifluoromethylbenzoyl)-2-(4-indanylamino)-2-imidazoline, melting point 183°–185° C.

EXAMPLE 61

1-(2,3-Dimethylbenzoyl)-2-(4-indanylamino)-2-imidazoline, melting point 186.5°–189° C.

Further examples are: 1-propionyl-2-(5,6,7,8-tetrahydro-1-naphthylamino)-2-imidazoline, 1-n-butyryl-2-(5,6,7,8-tetrahydro-1-naphthylamino)-2-imidazoline, 1-isobutyryl-2-(5,6,7,8-tetrahydro-1-naphthylamino)-2-imidazoline, 1-chloroacetyl-2-(4-indanylamino)-2-imidazoline, 1-trichloroacetyl-2-(4-indanylamino)-2-imidazoline, 1-phenoxyacetyl-2-(4-indanylamino)-2-imidazoline, 1-(o-toluoyl)-2-(5,6,7,8-tetrahydro-1-naphthylamino)-2-imidazoline, 1-(o-chlorobenzoyl)-2-(5,6,7,8-tetrahydro-1-naphthylamino)-2-imidazoline, 1-(2-chloro-6-methylbenzoyl)-2-(4-indanylamino)-2-imidazoline, 1-(2-chloro-6-methylbenzoyl-2-5,6,7,8-tetrahydro-1-naphthylamino)-2-imidazoline, 1-(2,6-dichlorobenzoyl)-2-(5,6,7,8-tetrahydro-1-naphthylamino)-2-imidazoline, 1-cyclopropylcarbonyl-2-(4-indanylamino)-2-imidazoline, 1-cyclopentylcarbonyl-2-(4-indanylamino)-2-imidazoline, 1-methoxycarbonyl-2-(5,6,7,8-tetrahydro-1-naphthylamino)-2-imidazoline, 1-ethoxycarbonyl-2-(5,6,7,8-tetrahydro-1-naphthylamino)-2-imidazoline, 1-isopropoxycarbonyl-2-(4-indanylamino)-2-imidazoline, 1-n-butyloxycarbonyl-2-(4-indanylamino)-2-imidazoline, 1-n-butyloxycarbonyl-2-(5,6,7,8-tetrahydro-1-naphthylamino)-2-imidazoline, 1-isobutyloxycarbonyl-2-(4-indanylamino)-2-imidazoline, 1-sec.-butyloxycarbonyl-2-(4-indanylamino)-2-imidazoline, 1-(2-ethylhexoxycarbonyl)-2-(4-indanylamino)-2-imidazoline, 1-(2-bromoethoxycarbonyl)-2-(4-indanylamino)-2-imidazoline, 1-(2-methoxyethoxycarbonyl)-2-(4-indanylamino)-2-imidazoline, 1-(2,2,2-trichloroethoxycarbonyl)-2-(4-indanylamino)-2-imidazoline, 1-cyclopentyloxycarbonyl-2-(4-indanylamino)-2-imidazoline, 1-cyclohexoxycarbonyl-2-(4-indanylamino)-2-imidazoline, 1-(p-tert.-butylcyclohexoxycarbonyl)-2-(4-indanylamino)-imidazoline, 1-(p-chlorobenzyloxycarbonyl)-2-(4-indanylamino)-2-imidazoline, 1-(p-methoxybenzyloxycarbonyl)-2-(4-indanylamino)-2-imidazoline, 1-(p-nitrobenzyloxycarbonyl)-2-(4-indanylamino)-2-imidazole, 1-allyloxycarbonyl-2-(4-indanylamino)-2-imidazoline, 1-(p-nitrophenoxycarbonyl)-2-(4-indanylamino)-2-imidazoline, 1-(o-chlorophenylacetyl)-2-(4-indanylamino)-2-imidazoline, 1-(m-chlorophenylacetyl)-2-(4-indanylamino)-2-imidazoline, 1-(3,4-dimethoxyphenylacetyl)-2-(4-indanylamino)-2-imidazoline and 1-(3-phenylpropionyl)-2-(4-indanylamino)-2-imidazoline.

Examples of deacylation reactions:

EXAMPLE 62

73.0 g (0.3 mole) of pure 1-acetyl-2-(4-indanylamino)-2-imidazoline obtained as described in Example 1, in 500 ml of water, are refluxed for 3 hours, while stirring. The mixture is allowed to cool to about 40°–45° C., 15% strength nitric acid (about 83 ml) is added dropwise, while stirring, until a neutral reaction persists, 6 g of active charcoal are added, and the mixture is again boiled briefly and filtered hot. After standing overnight in a refrigerator, 63.5 g (78.8% of theory) of pure 2-(4-indanylamino)-2-imidazoline nitrate of melting point 143°–144° C. crystalline from the filtrate.

EXAMPLE 63

500 ml of water are added to 90.2 g of the crude 1-acetyl-2-(4-indanylamino)-2-imidazoline obtained as described in Example 1, and the mixture is boiled for 4 hours while passing steam into it. On acidifying the steam distillate with hydrochloric acid, and evaporating to dryness, 43.6 g of 4-aminoindan hydrochloride are recovered. Using the method described in Example 62, the distillation residue is mixed with nitric acid and worked up. 43.5 g (68.5% of theory, based on 4-aminoindan converted) of 2-(4-indanylamino)-2-imidazoline nitrate of melting point 142°–143° C. are obtained.

COMPARATIVE EXAMPLE TO EXAMPLE 62

(according to the prior art, viz. German Laid-Open Application DOS No. 2,316,377, Example 1)

4.87 g (20 mmoles) of pure 1-acetyl-2-(4-indanylamino)-2-imidazoline, obtained as described in Example 1, in 40 ml of methanol are refluxed for 6 hours. The methanol is distilled off under reduced pressure, 40 ml of water are added to the oily residue and the mixture is neutralized with nitric acid, and worked up, by the method described in Example 62. 3.14 g (59.3% of theory) of 2-(4-indanylamino)-2-imidazoline nitrate of melting point 142°–143° C. are obtained.

EXAMPLE 64

11.2 g (43.6 mmoles) of 1-acetyl-2-(5,6,7,8-tetrahydro-1-naphthylamino)-2-imidazoline, obtained as described in Example 7, in 50 ml of water are refluxed for 3 hours. After stripping off the solvent, 9.2 g (98% of theory) of pure 2-(5,6,7,8-tetrahydro-1-naphthylamino)-2-imidazoline of melting point 142.5°–143.5° C. remain.

EXAMPLE 65

4.0 g (14.6 mmoles) of 1-ethoxycarbonyl-2-(4-indanylamino)-2-imidazoline, obtained as described in Example 6, in 40 ml of water are refluxed for 3 hours. About 5 ml of 15% strength HNO$_3$ are added to the reaction solution, which has been cooled to about 45° C. to bring the pH to 3, 0.3 g of active charcoal is added, the mixture is boiled briefly, filtered hot, cooled to room temperature and left to stand overnight in a refrigerator. The crystalline product which has separated out is filtered off and dried, giving 2.0 g (52% of theory) of pure 2-(4-indanylamino)-2-imidazoline nitrate of melting point 142°–143° C.

EXAMPLE 66

8.0 g (26.2 mmoles) of 1-benzoyl-2-(indanylamino)-2-imidazoline, obtained as described in Example 8, in 50 ml of water are refluxed for 3 hours and worked up as described in Example 65. 6.0 g (86.7% of theory) of 2-(4-indanylamino)-2-imidazoline nitrate of melting point 142°–143° C. are obtained.

COMPARATIVE EXAMPLE TO EXAMPLE 66

(according to the prior art, viz. German Laid-Open Application DOS 2,316,377)

8.0 g (26.2 mmoles) of 1-benzoyl-2-(4-indanylamino)-2-imidazoline in 40 ml of methanol are refluxed for 3 hours. The solvent is then stripped off under reduced pressure on a rotary evaporator, 50 ml of water are added to the residue and the latter is converted to the nitrate, and isolated, by the method described in Example 66. The product obtained is still yellow and has a melting point of 138.5°–139.5° C. After recrystallization from water, 1.8 g (26.0% of theory) of pure 2-(4-indanylamino)-2-imidazoline nitrate of melting point 142°–143° C. are obtained.

We claim:

1. A 1-acyl-2-imidazoline of the formula

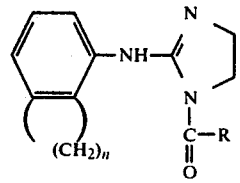

where n is 3 or 4 and R is hydrogen, alkyl of 1 to 4 carbon atoms (which is unsubstituted, or is monosubstituted, disubstituted or trisubstituted by halogen, alkoxy of 1 to 4 carbon atoms, alkoxycarbonyl, where alkyl is of 1 or 2 carbon atoms, or phenoxy), cycloalkyl of 3 to 7 carbon atoms in the ring, alkoxy (where alkyl is of 1 to 8 carbon atoms, and which is unsubstituted or monosubstituted, disubstituted or trisubstituted by halogen, or monosubstituted by alkoxy of 1 to 4 carbon atoms), cycloalkoxy of 3 to 10 carbon atoms in the ring (which is unsubstituted or substituted by alkyl of 1 to 4 carbon atoms), alkenyloxy of 3 or 4 carbon atoms, alkoxycarbonyl, where alkyl is of 1 or 2 carbon atoms, benzyloxy, methoxybenzyloxy, chlorobenzyloxy, nitrobenzyloxy, phenoxy, nitrophenoxy, phenyl and phenylalkyl of 7 or 8 carbon atoms (where phenyl is unsubstituted or monosubstituted, disubstituted or trisubstituted by alkyl of 1 to 4 carbon atoms, trifluoromethyl, halogen, alkoxy of 1 to 4 carbon atoms, methylenedioxy, ethylenedioxy or phenyl), phenylalkenyl of 8 or 9 carbon atoms (which is unsubstituted or monosubstituted, disubstituted or trisubstituted by halogen, or alkoxy of 1 to 4 carbon atoms), thienyl, furyl, pyridyl or chloropyridyl.

2. A 1-acyl-2-imidazoline of the formula I, where n is 3 or 4 and R is alkyl of 1 to 4 carbon atoms, alkoxy of 1 to 8 carbon atoms or phenyl.

3. 1-Acetyl-2-(4-indanylamino)-2-imidazoline.

4. 1-Acetyl-2-(5,6,7,8-tetrahydro-1-naphthylamino)-2-imidazoline.

5. 1-Ethoxycarbonyl-2-(4-indanylamino)-2-imidazoline.

6. 1-Benzoyl-2-(4-indanylamino)-2-imidazoline.

* * * * *